(12) United States Patent
Sun et al.

(10) Patent No.: US 10,301,344 B2
(45) Date of Patent: May 28, 2019

(54) L-PROLINE COMPLOF SODIUM-GLUCOSE COTRANSPORTER 2 INHIBITOR, MONOHYDRATE AND CRYSTAL FORM THEREOF

(71) Applicant: Jiangsu Hengrui Medicine Co., Ltd., Lianyungang, Jiangsu (CN)

(72) Inventors: Piaoyang Sun, Jiangsu (CN); Guaili Wu, Jiangsu (CN); Changshan Guo, Jiangsu (CN); Yun Lu, Jiangsu (CN); Yuxia Wu, Jiangsu (CN); Lingjia Shen, Jiangsu (CN)

(73) Assignee: Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 15/514,118

(22) PCT Filed: Sep. 8, 2015

(86) PCT No.: PCT/CN2015/089128
§ 371 (c)(1),
(2) Date: Mar. 24, 2017

(87) PCT Pub. No.: WO2016/050134
PCT Pub. Date: Apr. 7, 2016

(65) Prior Publication Data
US 2017/0298087 A1    Oct. 19, 2017

(30) Foreign Application Priority Data
Sep. 30, 2014 (CN) .......................... 2014 1 0523436

(51) Int. Cl.
| | | |
|---|---|---|
| *C07H 1/00* | (2006.01) | |
| *C07H 9/04* | (2006.01) | |
| *C07H 19/01* | (2006.01) | |
| *C07D 207/16* | (2006.01) | |

(52) U.S. Cl.
CPC .......... *C07H 19/01* (2013.01); *C07D 207/16* (2013.01); *C07H 1/00* (2013.01); *C07H 9/04* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 2013/0130997 A1* | 5/2013 | Yang | ........................ C07H 7/04 514/25 |
| 2014/0303096 A1* | 10/2014 | Reiche | ................. C07H 15/207 514/23 |

FOREIGN PATENT DOCUMENTS

| | | |
|---|---|---|
| CN | 102149717 A | 8/2011 |
| CN | 102372722 A | 3/2012 |
| CN | 104017031 A | 9/2014 |
| CN | 104031098 A | 9/2014 |
| WO | 2012019496 A1 | 2/2012 |
| WO | WO-2014016381 A1 * | 1/2014 ............. C07H 15/26 |

OTHER PUBLICATIONS

Int'l Search Report dated Nov. 26, 2015 in Int'l Application No. PCT/CN2015/089128.

* cited by examiner

*Primary Examiner* — Layla D Berry
(74) *Attorney, Agent, or Firm* — Panitch Schwarze Belisario & Nadel LLP

(57) ABSTRACT

Provided are an L-proline complex of a sodium-glucose cotransporter 2 inhibitor, and a monohydrate and a crystal of the L-proline complex. Specifically, provided are 1,6-dehydrated-1-C{4-chloro-3-[(3-fluoro-4-ethoxyphenyl)methyl]phenyl}-5-C-(hydroxymethyl)-β-L-idopyranose L-proline (a compound of formula (I)), a monohydrate and a type A crystal thereof, and a preparation method therefor. The obtained type A crystal of the compound of formula (I) has good chemical stability and crystal stability, and the crystallization solvent used has low toxicity and low residue, so the type A crystal can be better used in clinical treatment.

17 Claims, 8 Drawing Sheets (I)

L-PROLINE COMPLEX OF SODIUM-GLUCOSE COTRANSPORTER 2 INHIBITOR, MONOHYDRATE AND CRYSTAL FORM THEREOF

CROSS-REFERENCE TO RELATED APPLICATIONS

This application is a Section 371 of International Application No. PCT/CN2015/089128, filed Sep. 8, 2015, which was published in the Chinese language on Apr. 7, 2016, under International Publication No. WO 2016/050134 A1 and the disclosure of which is incorporated herein by reference.

FIELD OF THE INVENTION

The invention relates to a 1,6-anhydro-1-C-{4-chloro-3-[(3-fluoro-4-ethoxyphenyl)methyl]phenyl}-5-C-(hydroxymethyl)-β-L-idopyranose L-proline complex, a monohydrate and a crystal form A thereof.

BACKGROUND OF THE INVENTION

With the socio-economic development and the improvement of material living standards, the number of diabetics on a global scale is increasing rapidly. Diabetes is usually divided into two types, such as type I and type II, in which more than 90% of diabetes is type II. Many types of diabetes drugs are already commercially available, but so far no drug has been able to single-handedly keep the blood glucose levels of patients with type II diabetes within the target range for a long time. In recent years, more and more approaches for the treatment of type II diabetes are provided due to the in-depth study of the pathogenesis of diabetes. The discovery of sodium-glucose cotransporter 2 (SGLT-2) inhibitors provides another new idea for the treatment of diabetes. The mechanism of action of SGLT-2 inhibitors is to selectively inhibit the activity of SGLT-2, thereby reducing blood glucose. SGLT-2 is selected as a target spot, on one hand because of its absolute reabsorption of glucose, and on the other hand because it is only expressed in the kidney. The current study also finds that the mechanism of action of SGLT-2 does not depend on the dysfunction of β cells or the degree of insulin resistance, and its effect is not decreased with function failure of β-cell or severe insulin resistance. Therefore, it is reasonable to believe that the use of SGLT-2 inhibitors in the current treatment of type II diabetes has a promising future.

WO2012019496 discloses a SGLT-2 inhibitor having the following formula, whose chemical name is 1,6-anhydro-1-C-{4-chloro-3-[(3-fluoro-4-ethoxyphenyl)methyl]phenyl}-5-C-(hydroxymethyl)-β-L-idopyranose.

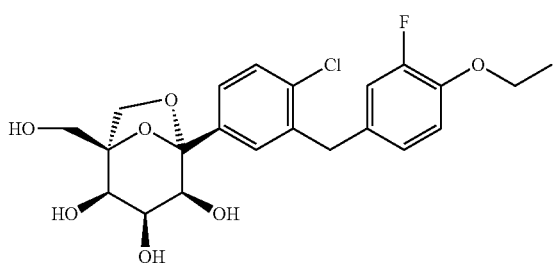

However, it is impractical to directly use 1,6-anhydro-1-C-{4-chloro-3-[(3-fluoro-4-ethoxyphenyl)methyl]phenyl}-5-C-(hydroxymethyl)-β-L-idopyranose as a pharmaceutically active ingredient due to its poor development form resulting from the lower melting point (83° C.) and hygroscopic properties. Therefore, it is important to develop a stable form of the compound.

The crystal structure of the pharmaceutically active ingredient often affects the chemical stability of the drug. Different crystallization conditions and storage conditions may lead to changes in the crystal structure of the compound, and sometimes may be accompanied with the production of other crystal forms. In general, an amorphous drug product does not have a regular crystal structure, and often has other defects, such as poor product stability, smaller particle size, difficult filtration, easy agglomeration, and poor liquidity. Thus, it is necessary to improve the various properties of the above product. There is a need to identify a new crystal form with high purity and good chemical stability.

SUMMARY OF THE INVENTION

The invention provides an L-proline complex of 1,6-anhydro-1-C-{4-chloro-3-[(3-fluoro-4-ethoxyphenyl)methyl]phenyl}-5-C-(hydroxymethyl)-β-L-idopyranose represented by formula (I):

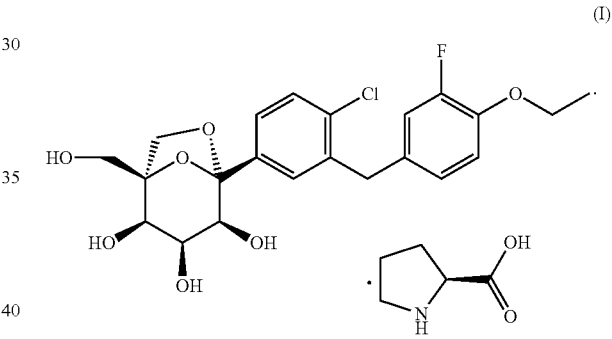

(I)

The complex of formula (I) can be prepared by co-crystallization of 1,6-anhydro-1-C-{4-chloro-3-[(3-fluoro-4-ethoxyphenyl)methyl]phenyl}-5-C-(hydroxymethyl)-β-L-idopyranose with L-proline. The invention provides a preparation method of the complex of formula (I), comprising a step of co-crystallizing 1,6-anhydro-1-C-{4-chloro-3-[(3-fluoro-4-ethoxyphenyl)methyl]phenyl}-5-C-(hydroxymethyl)-β-L-idopyranose with L-proline, wherein the molar ratio of L-proline to 1,6-anhydro-1-C-{4-chloro-3-[(3-fluoro-4-ethoxyphenyl)methyl]phenyl}-5-C-(hydroxymethyl)-β-L-idopyranose added for co-crystallization is less than to 2:1, preferably from 2:1 to 0.1:1, more preferably from 1.5:1 to 0.5:1, and most preferably from 1.5:1 to 1:1 or from 1.2:1 to 0.8:1.

In comparison to 1,6-anhydro-1-C-{4-chloro-3-[(3-fluoro-4-ethoxyphenyl)methyl]phenyl}-5-C-(hydroxymethyl)-β-L-idopyranose, the complex of formula (I) has a higher melting point and improved stability.

In another aspect, the invention provides a monohydrate of the complex of formula (I) and crystal form A thereof.

A series of crystal products of the complex of formula (I) obtained under various crystallization conditions were subjected to X-ray diffraction and differential scanning calorimetry (DSC) measurement. It was found that a stable crystal form of the complex of formula (I), which is referred to as crystal form A, can be obtained under the normal crystallization condition. The DSC spectrum of crystal form A according to the present application shows a melting endothermic peak at about 109.51° C. The X-ray powder diffraction spectrum of crystal form A, which is obtained by using Cu-Kα radiation and represented by 2θ angle and interplanar distance (d value), is shown in FIG. 1 in which there are characteristic peaks at 5.50 (16.07), 7.82 (11.30), 8.64 (10.22), 10.33 (8.55), 12.18 (7.26), 12.49 (7.08), 14.47 (6.11), 15.51 (5.71), 15.89 (5.57), 17.28 (5.13), 18.89 (4.70), 19.39 (4.58), 20.40 (4.35), 22.85 (3.89), 23.89 (3.72), 25.93 (3.43), 27.66 (3.22), 28.97 (3.08) and 31.16 (2.87).

The invention further provides a preparation method of crystal form A of a monohydrate of 1,6-anhydro-1-C-{4-chloro-3-[(3-fluoro-4-ethoxyphenyl)methyl]phenyl}-5-C-(hydroxymethyl)-β-L-idopyranose L-proline, comprising the following steps of:

(1) dissolving 1,6-anhydro-1-C-{4-chloro-3-[(3-fluoro-4-ethoxyphenyl)methyl]phenyl}-5-C-(hydroxymethyl)-β-L-idopyranose and L-proline in a solvent, then cooling the reaction solution to precipitate a crystal, wherein the solvent is selected from the group consisting of an organic solvent and a mixed solvent of an organic solvent and water; the organic solvent is one or more selected from the group consisting of alcohols, ketones, esters, ethers, hydrocarbons and nitriles having 6 or less carbon atoms; and (2) filtering the crystal, then washing and drying it;

preferably, wherein the molar ratio of L-proline and 1,6-anhydro-1-C-{4-chloro-3-[(3-fluoro-4-ethoxyphenyl)methyl]phenyl}-5-C-(hydroxymethyl)-β-L-idopyranose added in step (1) is less than to 2:1, preferably from 2:1 to 0.1:1, more preferably from 1.5:1 to 0.5:1, and most preferably from 1.5:1 to 1:1 or from 1.2:1 to 0.8:1.

In a preferred embodiment of the invention, the organic solvent is selected from the group consisting of alcohols, ketones, and esters having 3 or less carbon atoms; or a mixed solvent of one or more of the above solvents and halogenated hydrocarbons having 3 or less carbon atoms. More preferably, the organic solvent is selected from methanol, ethanol, and isopropanol; or methanol/water, ethanol/water, isopropanol/water or ethanol/n-hexane.

Most preferably, the single solvent is ethanol.

In one preferred embodiment of the invention, the mixed solvent is a mixed solvent of ethanol/water, and the ratio of the two is not particularly limited. In a preferred embodiment of the present invention, the volume ratio of ethanol/water is 19:1.

The recrystallization method is not particularly limited and can be carried out by a conventional recrystallization process. For example, the raw material i.e., the complex of formula (I) can be dissolved in an organic solvent under heating, and then the solution is cooled slowly to precipitate a crystal. After the completion of crystallization, the resulting product is filtered and dried to obtain the desired crystal. In particular, the crystal obtained by filtration is usually vacuum-dried under reduced pressure at about 20 to 60° C., preferably at room temperature, to remove the recrystallization solvent.

The crystal form of the obtained complex of formula (I) was determined by differential scanning calorimetry (DSC) and X-ray diffraction spectrum. Meanwhile, the residual solvent of the obtained crystal was also determined.

Crystal form A of the complex of formula (I) prepared according to the method of the invention does not contain or contains only a relatively low content of residual solvent, which meets the requirement of the national pharmacopoeia concerning the limitation of the residual solvent of drug products. Thus, the crystal of the invention is suitable for use as a pharmaceutically active ingredient.

It has been shown that the stability of crystal form A of the complex of formula (I) prepared by the invention is significantly better than that of the amorphous sample under the conditions of high temperature and high humidity. Moreover, crystal form A has good stability under the conditions of grinding, pressure and heating, which meets the production, transportation and storage requirements of drug products. The preparation process of crystal form A is stable, repeatable and controlled, and is suitable for industrial production.

DETAILED DESCRIPTION OF THE INVENTION

The following examples serve to illustrate the invention in more detail, but the examples of the invention are only intended to describe the technical solution of the invention, and should not be considered as limiting the spirit and the scope of the invention.

Test instruments used in the experiments

1. DSC spectrum

Instrument type: Mettler Toledo DSC 1 Stare$^e$ System

Purging gas: Nitrogen

Heating rate: 10.0° C./min

Temperature range: 40-200° C.

2. X-ray diffraction spectrum

Instrument type: Bruker D8 Focus X-ray powder diffractometer

Rays: monochromatic Cu-Kα rays (λ=1.5406 Å)

Scanning mode: θ/2θ, Scanning range: 2-40°

Voltage: 40 KV Electric Current: 40 mA

EXAMPLE 1

Figure 1:
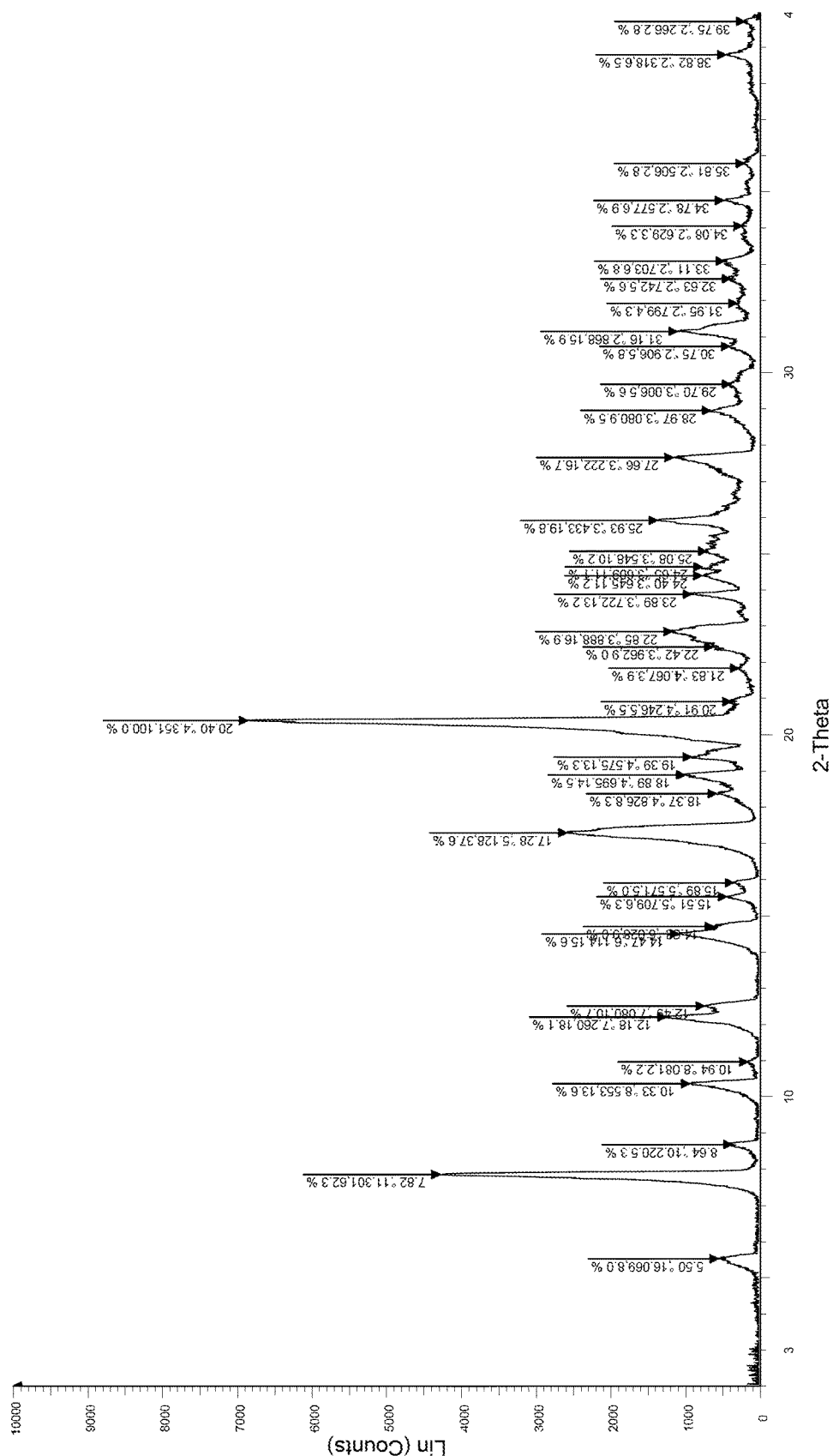
FIG. 1 shows the X-ray powder diffraction spectrum of crystal form A of the complex of formula (I)
Figure 2:
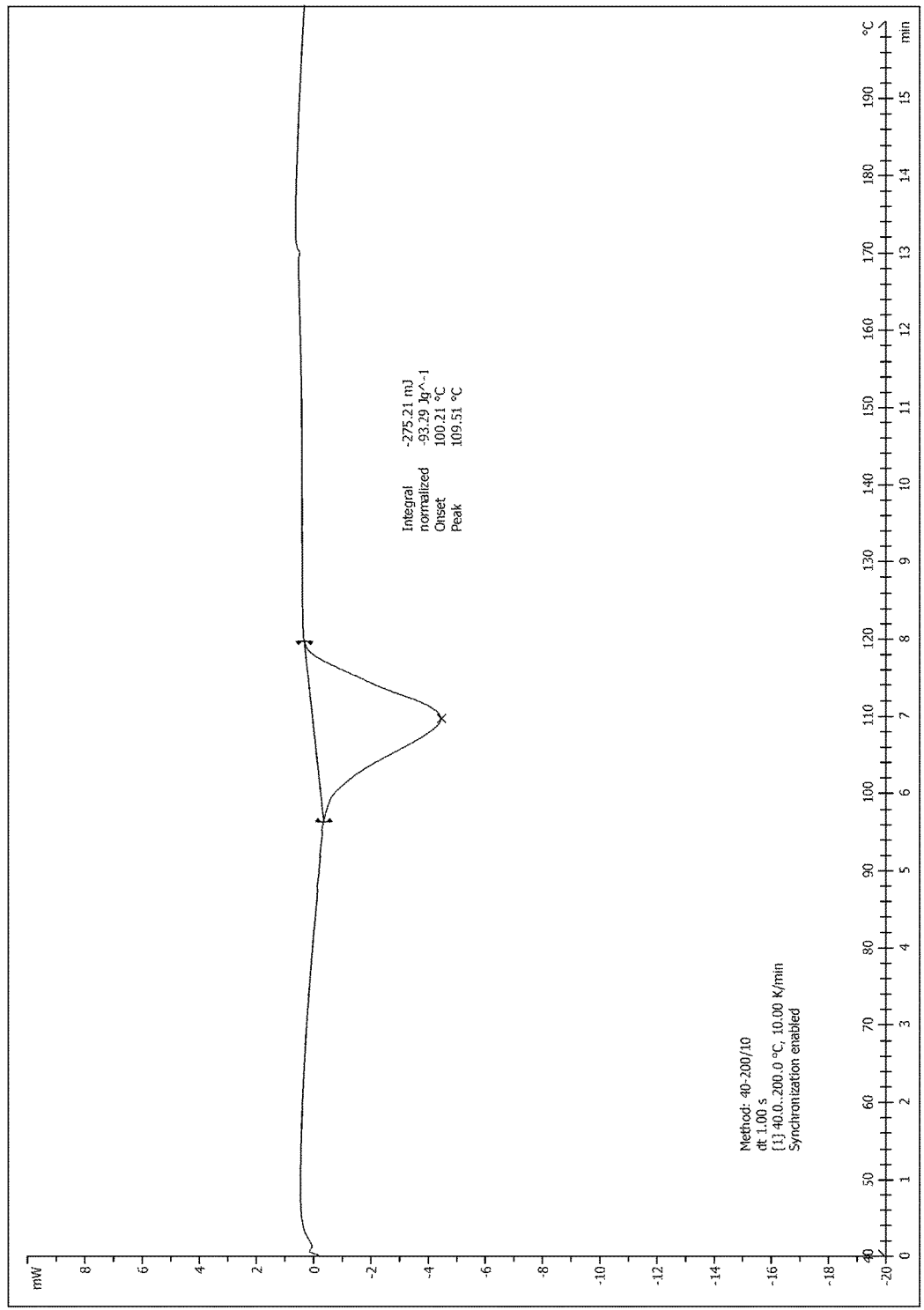
FIG. 2 shows the DSC spectrum of crystal form A of the complex of formula (I)

1.0 g (2.2 mmol) of 1,6-anhydro-1-C-{4-chloro-3-[(3-fluoro-4-ethoxyphenyl)methyl]phenyl}-5-C-(hydroxymethyl)-β-L-idopyranose (prepared according to the method disclosed in WO2012019496) was dissolved in 7.20 g of ethanol with stirring. 0.2786 g of L-proline (2.42 mmol, 1.1 eq) was added into the solution at room temperature. The mixture was stirred and heated to reflux for 10 minutes until the reaction solution became clear, then filtered while it was hot. The filtrate was cooled to room temperature with stirring. A large amount of white solid was precipitated. The mixture was left overnight, then filtered and dried to obtain 1.14 g of the complex of formula (I) as a white solid in 88% yield. The X-ray diffraction spectrum of this crystal sample is shown in FIG. 1 in which there are characteristic peaks at 5.50 (16.07), 7.82 (11.30), 8.64 (10.22), 10.33 (8.55), 12.18 (7.26), 12.49 (7.08), 14.47 (6.11), 15.51 (5.71), 15.89 (5.57), 17.28 (5.13), 18.89 (4.70), 19.39 (4.58), 20.40 (4.35), 22.85 (3.89), 23.89 (3.72), 25.93 (3.43), 27.66 (3.22), 28.97 (3.08) and 31.16 (2.87). The DSC spectrum of this crystal sample is shown in FIG. 2, which has a melting endothermic peak at 109.5° C. This crystal form was defined as crystal form A.

EXAMPLE 2

1.0 g (2.2 mmol) of 1,6-anhydro-1-C-{4-chloro-3-[(3-fluoro-4-ethoxyphenyl)methyl]phenyl}-5-C-(hydroxymethyl)-β-L-idopyranose (prepared according to the method disclosed in WO2012019496) was dissolved in 8 mL of methanol/water (V:V=1:1) with stirring. Then, 0.38 g of L-proline (3.3 mmol, 1.5 eq) was added into the solution at room temperature. The mixture was stirred and heated to reflux for 10 minutes until the reaction solution became clear, then filtered while it was hot. The filtrate was cooled to room temperature with stirring. A large amount of white solid was precipitated. The mixture was left overnight, then filtered and dried to obtain 1.08 g of the complex of formula (I) as a white solid in 83.1% yield. The product was identified as crystal form A after studying and comparing the X-ray diffraction and DSC spectra.

EXAMPLE 3

1.0 g (2.2 mmol) of 1,6-anhydro-1-C-{4-chloro-3-[(3-fluoro-4-ethoxyphenyl)methyl]phenyl}-5-C-(hydroxymethyl)-β-L-idopyranose (prepared according to the method disclosed in WO2012019496) was dissolved in 10 mL of isopropanol/water (V:V=1:1) with stirring. Then, 0.25 g of L-proline (2.2 mmol, 1.0 eq) was added into the solution at room temperature. The mixture was stirred and heated to reflux for 10 minutes until the reaction solution became clear, then filtered while it was hot. The filtrate was cooled to room temperature with stirring. A large amount of white solid was precipitated. The mixture was left overnight, then filtered and dried to obtain 1.10 g of the complex of formula (I) as a white solid in 84.6% yield. The X-ray diffraction spectrum of this crystal sample is shown in FIG. 1. The product was identified as crystal form A after studying and comparing the X-ray diffraction and DSC spectra.

EXAMPLE 4

Figure 3:
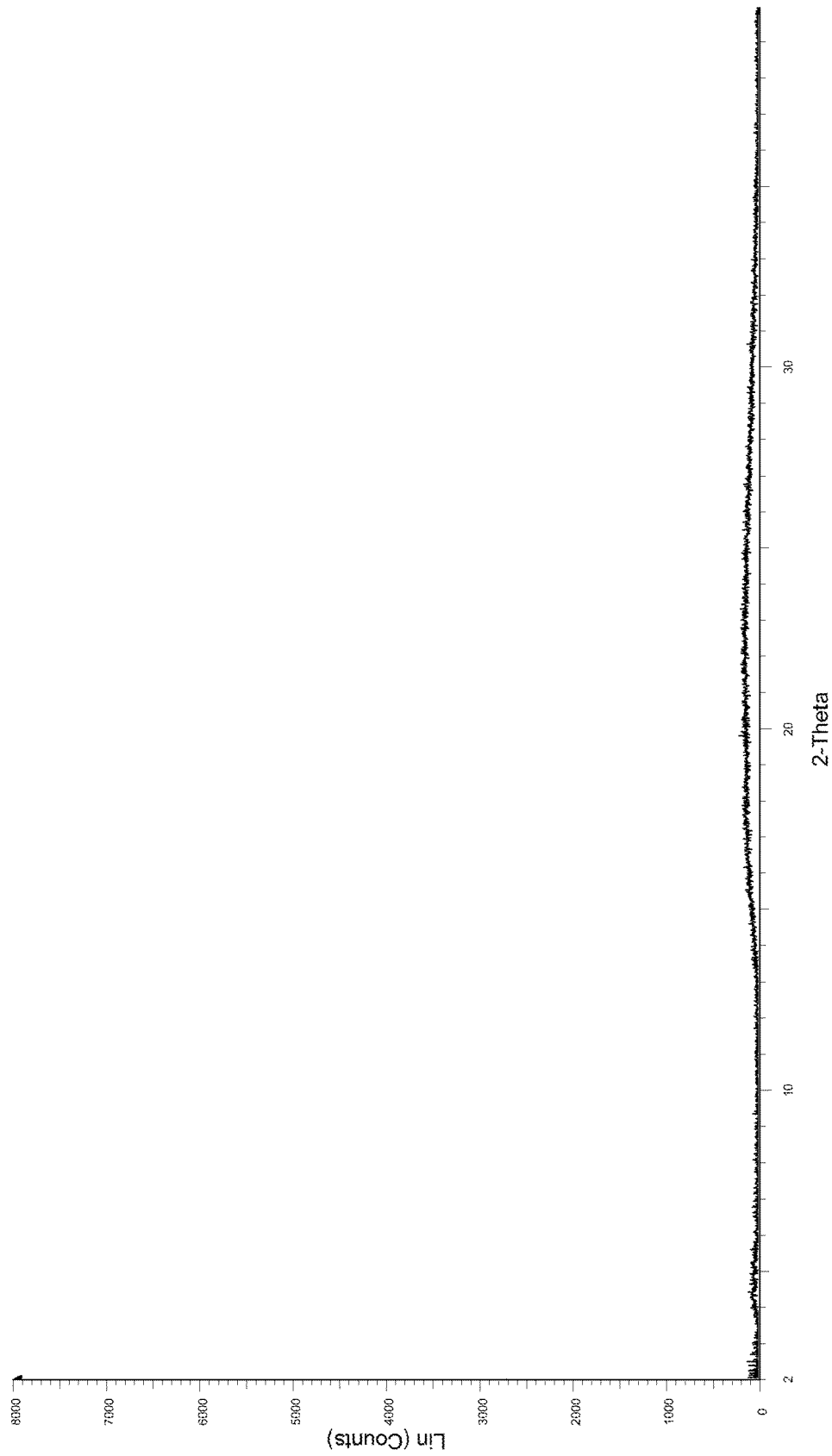
FIG. 3 shows the X-ray powder diffraction spectrum of the amorphous solid of the complex of formula (I)
Figure 4:
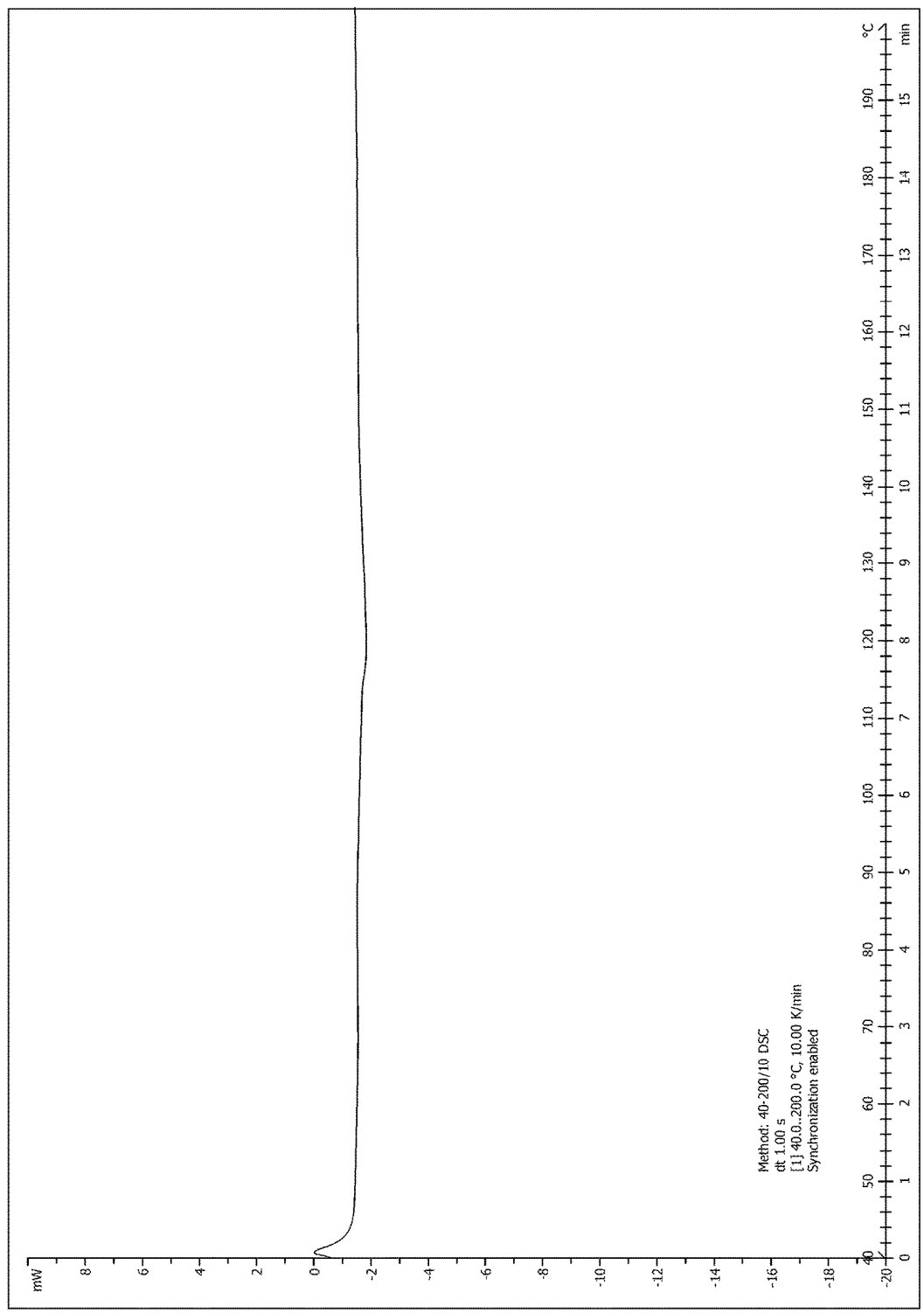
FIG. 4 shows the DSC spectrum of the amorphous solid of the complex of formula (I)

1.0 g (1.7 mmol) of the complex of formula (I) (prepared according to Example 1) was added to a 250 ml one-necked flask and dissolved in 160 ml of water under heating. The solution was refluxed for 10 minutes, then cooled and left to stand for precipitation. The resulting precipitate was collected by filtration and dried to obtain 336 mg of an off white solid in 33.6% yield. The X-ray diffraction spectrum of this solid sample is shown in FIG. 3 in which there are no characteristic peaks of a crystal. The DSC spectrum of this solid sample is shown in FIG. 4, which has no melting absorption peak below 200° C. The product was thus identified as an amorphous solid.

EXAMPLE 5

1.0 g (1.7 mmol) of the complex of formula (I) (prepared according to Example 1) was added to a 25 ml one-necked flask and dissolved in 2 ml of ethanol under heating. The solution was refluxed for 10 minutes, then cooled and left to stand for precipitation. The resulting precipitate was collected by filtration and dried to obtain 728 mg of a white solid in 72.8% yield. The product was identified as crystal form A after studying and comparing the X-ray diffraction and DSC spectra.

EXAMPLE 6

1.0 g (1.7 mmol) of the complex of formula (I) (prepared according to Example 1) was added to a 25 ml one-necked flask and dissolved in 2 ml of methanol under heating. The solution was refluxed for 10 minutes, then cooled and left to stand for precipitation. The resulting precipitate was collected by filtration and dried to obtain 643 mg of a white solid in 64.3% yield. The product was identified as crystal form A after studying and comparing the X-ray diffraction and DSC spectra.

EXAMPLE 7

1.0 g (1.7 mmol) of the complex of formula (I) (prepared according to Example 1) was added to a 25 ml one-necked flask and dissolved in 2 ml of 50% methanol under heating. The solution was refluxed for 10 minutes, then cooled and left to stand for precipitation. The resulting precipitate was collected by filtration and dried to obtain 602 mg of a white solid in 60.2% yield. The product was identified as crystal form A after studying and comparing the X-ray diffraction and DSC spectra.

EXAMPLE 8

1.0 g (1.7 mmol) of the complex of formula (I) (prepared according to Example 1) was added to a 25 ml one-necked flask and dissolved in 2 ml of isopropanol under heating. The solution was refluxed for 10 minutes, then cooled and left to stand for precipitation. The resulting precipitate was collected by filtration and dried to obtain 740 mg of a white solid in 74.0% yield. The product was identified as crystal form A after studying and comparing the X-ray diffraction and DSC spectra.

EXAMPLE 9

1.0 g (1.7 mmol) of the complex of formula (I) (prepared according to Example 1) was added to a 25 ml one-necked flask and dissolved in 2 ml of 50% ethanol under heating. The solution was refluxed for 10 min, then cooled and left to stand for precipitation. The resulting precipitate was collected by filtration and dried to obtain 595 mg of a white solid in 59.5% yield. The product was identified as crystal form A after studying and comparing the X-ray diffraction and DSC spectra.

EXAMPLE 10

1.0 g (1.7 mmol) of the complex of formula (I) (prepared according to Example 1) was added to a 25 ml one-necked flask and dissolved in 2 ml of 95% ethanol under heating. The solution was refluxed for 10 min, then cooled and left to stand for precipitation. The resulting precipitate was collected by filtration and dried to obtain 813 mg of a white solid in 81.3% yield. The product was identified as crystal form A after studying and comparing the X-ray diffraction and DSC spectra.

EXAMPLE 11

1.0 g (1.7 mmol) of the complex of formula (I) (prepared according to Example 1) was added to a 25 ml one-necked flask and dissolved in 3 ml of ethanol/n-hexane (V:V=3:1) under heating. The solution was refluxed for 10 minutes, then cooled and left to stand for precipitation. The resulting precipitate was collected by filtration and dried to obtain 804 mg of a white solid in 80.4% yield. The product was identified as crystal form A after studying and comparing the X-ray diffraction and DSC spectra.

EXAMPLE 12

1.0 g (1.7 mmol) of the complex of formula (I) (prepared according to Example 1) was added to a 250 ml one-necked flask and dissolved in 94 ml of 10% ethanol under heating. The solution was refluxed for 10 minutes, then cooled and left to stand for precipitation. The resulting precipitate was collected by filtration and dried to obtain 338 mg of a white solid in 33.8% yield. The product was identified as crystal form A after studying and comparing the X-ray diffraction and DSC spectra.

EXAMPLE 13

Crystal form A prepared in Example 1 and the amorphous sample prepared in Example 4 were spread flat in the air to test their stability under the conditions of lighting (4500 Lux), heating (40° C., 60° C.), and high humidity (RH 75%, RH 90%). Sampling times of 5 days and 10 days were studied, and the purity as detected by HPLC is shown in Table 1.

TABLE 1

Comparison of stability of crystal form A and amorphous sample of the complex of formula (I)

| Batch number | Time (Day) | Lighting | 40° C. | 60° C. | RH 75% | RH 90% |
| --- | --- | --- | --- | --- | --- | --- |
| Crystal form A | 0 | 99.76% | 99.76% | 99.76% | 99.76% | 99.76% |
| S1052110422 | 5 | 99.76% | 99.76% | 99.74% | 99.75% | 99.76% |
|  | 10 | 99.76% | 99.75% | 99.74% | 99.74% | 99.75% |

TABLE 1-continued

Comparison of stability of crystal form A and amorphous sample of the complex of formula (I)

| Batch number | Time (Day) | Lighting | 40° C. | 60° C. | RH 75% | RH 90% |
| --- | --- | --- | --- | --- | --- | --- |
| Amorphous | 0 | 99.68% | 99.68% | 99.68% | 99.68% | 99.68% |
| 20140411 | 5 | 99.60% | 99.65% | 99.67% | 99.66% | 99.66% |
|  | 10 | 99.55% | 99.62% | 99.56% | 99.65% | 99.64% |

After crystal form A and the amorphous sample were spread flat in the air to test the stability under the conditions of lighting, high temperature, high humidity, the results of the stability study showed that high humidity does not have much effect on the two examples, but under the conditions of lighting and high temperature, the stability of crystal form A is significantly better than that of the amorphous sample.

EXAMPLE 14

Crystal form A of the complex of formula (I) prepared according to the method of Example 1 was grinded, heated and pressed. The results showed that the crystal form was stable and the detailed experimental data are shown in Table 2 below.

TABLE 2

Stability study of crystal form A of the complex of formula (I)

| Batch number | Treatment process | Experiment procedure | Crystal form | DSC peak |
| --- | --- | --- | --- | --- |
| Experiment 14.1 20140415G | Grinding treatment for 10 min | 1.0 g of crystal form A of the complex of formula (I) was grinded for 10 min in a mortar under nitrogen atmosphere. | crystal form A | DSC peak 110.46° C. |
| Experiment 14.2 20140415H | Heating treatment at 60° C. for 3 hours | 1.0 g of crystal form A of the complex of formula (I) was spread flat and heated at 60° C. for 3 hours | crystal form A | DSC peak 110.64° C. |
| Experiment 14.3 20140415P | Pressing treatment | Crystal form A of the complex of formula (I) was pressed to a slice | crystal form A | DSC peak 110.29° C. |

EXAMPLE 15

Figure 5:
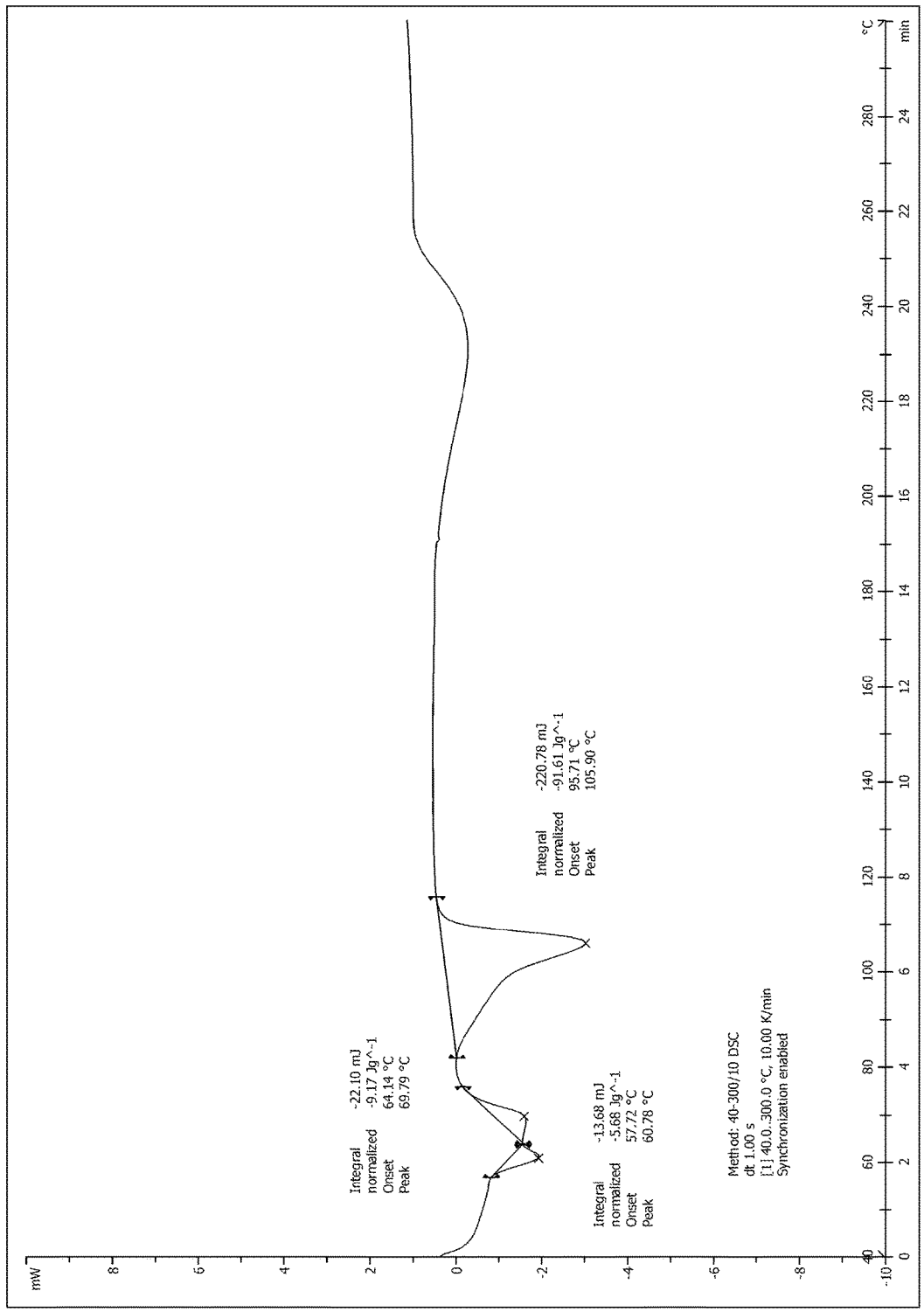
FIG. 5 shows the DSC spectrum of the solid prepared in Example 15 with 1,6-anhydro-1-C-{4-chloro-3-[(3-fluoro-4-ethoxyphenyl)methyl]phenyl}-5-C-(hydroxymethyl)-β-L-idopyranose/L-proline ratio of 1:2.
Figure 6:
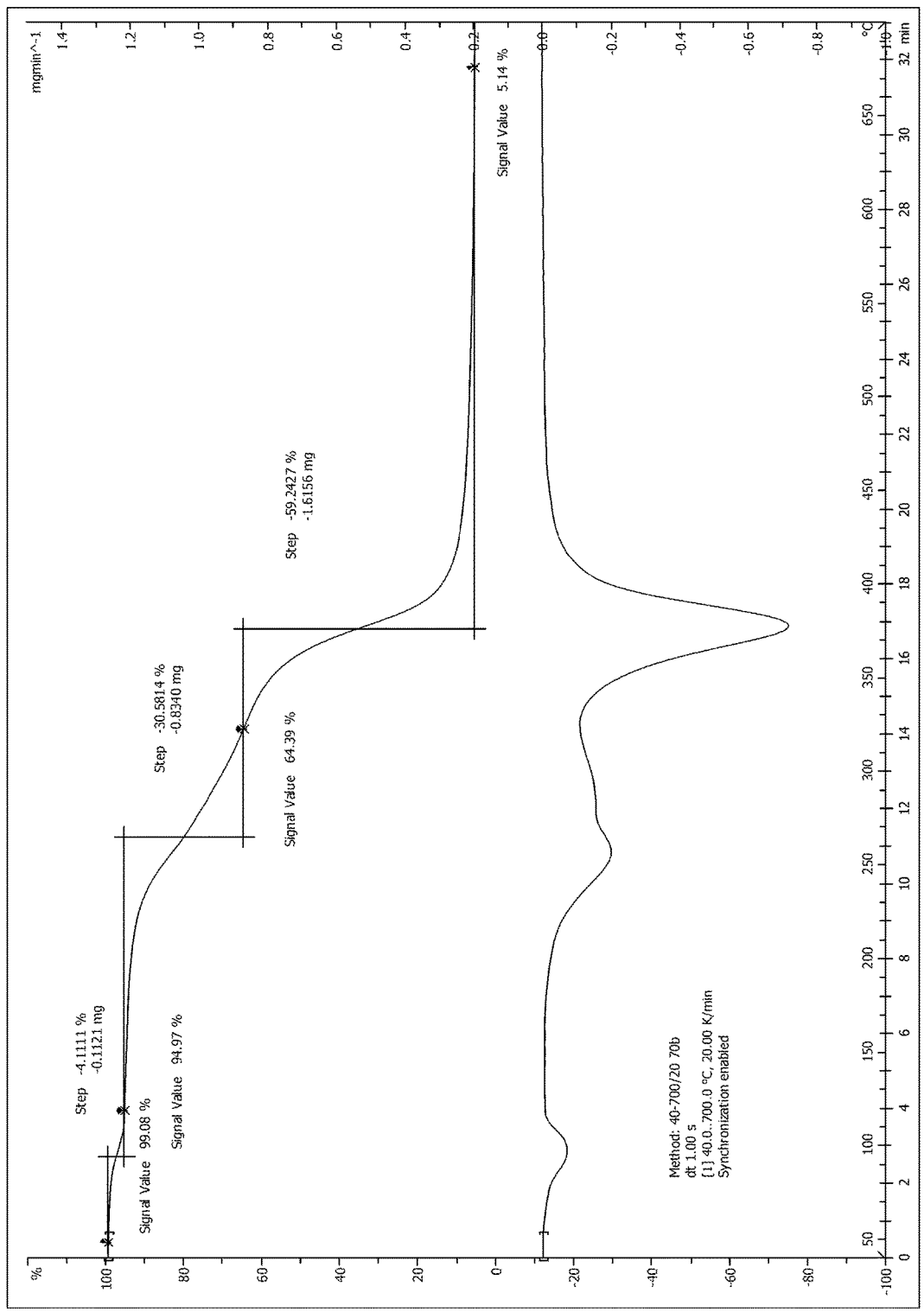
FIG. 6 shows the Thermo Gravimetric Analyzer (TGA) spectrum of the solid prepared in Example 15 with 1,6-anhydro-1-C-{4-chloro-3-[(3-fluoro-4-ethoxyphenyl)methyl]phenyl}-5-C-(hydroxymethyl)-β-L-idopyranose/L-proline ratio of 1:2.

According to the same method disclosed in Example 15 of CN104031098A, 0.23 g (2 mmol) of L-proline was dissolved in 1.2 mL of 90% ethanol/water, the solution was heated to a low boil, then a solution of 1,6-anhydro-1-C-{4-chloro-3-[(3-fluoro-4-ethoxyphenyl)methyl]phenyl}-5-C-(hydroxymethyl)-β-L-idopyranose (0.5 mmol) in 4 mL of ethanol was added. Acetone was slowly added to 10% of the total volume, the resulting solution was cooled to −20° C. for 2 hours, and a solid was formed during this time. The mixture was left for 2 days at room temperature. The container was centrifuged, and the supernatant was removed. The remaining solid was washed with n-hexane and dried under vacuum to obtain a white solid. HPLC analysis showed that the molar ratio of 1,6-anhydro-1-C-{4-chloro-3-[(3-fluoro-4-ethoxyphenyl)methyl]phenyl}-5-C-(hydroxymethyl)-β-L-idopyranose to L-proline is about 0.46 in the white crystalline solid. DSC and TGA spectra of the resulting solid were shown in FIG. 5 and FIG. 6, respectively. The DSC spectrum showed that the resulting solid had three endothermic peaks at 60.78° C., 69.79° C. and 105.90° C., which suggested that this substance might be unstable and that it was possible to produce degradation at lower temperatures, thereby leading to the loss of proline from the co-crystal. The TGA spectrum showed that the weight loss of proline in the solid is 30.58% (the theoretical value is 33.4% when the molar ratio of 1,6-anhydro-1-C-{4-chloro-3-[(3-fluoro-4-ethoxyphenyl)methyl]phenyl}-5-C-(hydroxymethyl)-β-L-idopyranose to L-proline is 1:2). The analysis of the HPLC, DSC, and TGA results indicated that the molar ratio of 1,6-anhydro-1-C-{4-chloro-3-[(3-fluoro-4-ethoxyphenyl)methyl]phenyl}-5-C-(hydroxymethyl)-β-L-idopyranose to L-proline in the resulting solid product is 1:2, and the stability of the resulting product was poor.

EXAMPLE 16

Figure 7:
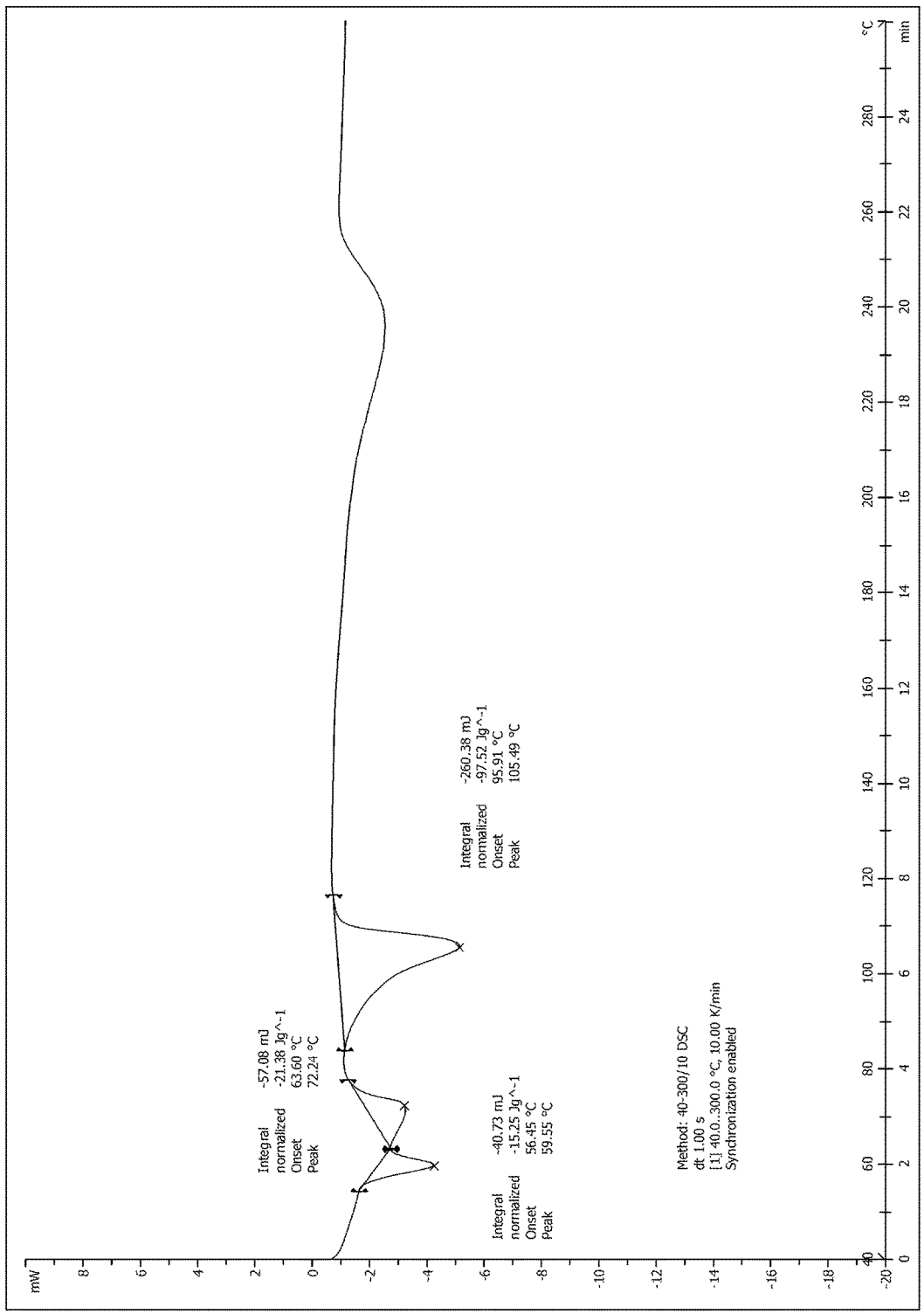
FIG. 7 shows the DSC spectrum of the solid prepared in Example 16 with 1,6-anhydro-1-C-{4-chloro-3-[(3-fluoro-4-ethoxyphenyl)methyl]phenyl}-5-C-(hydroxymethyl)-β-L-idopyranose/L-proline ratio of 1:2.
Figure 8:
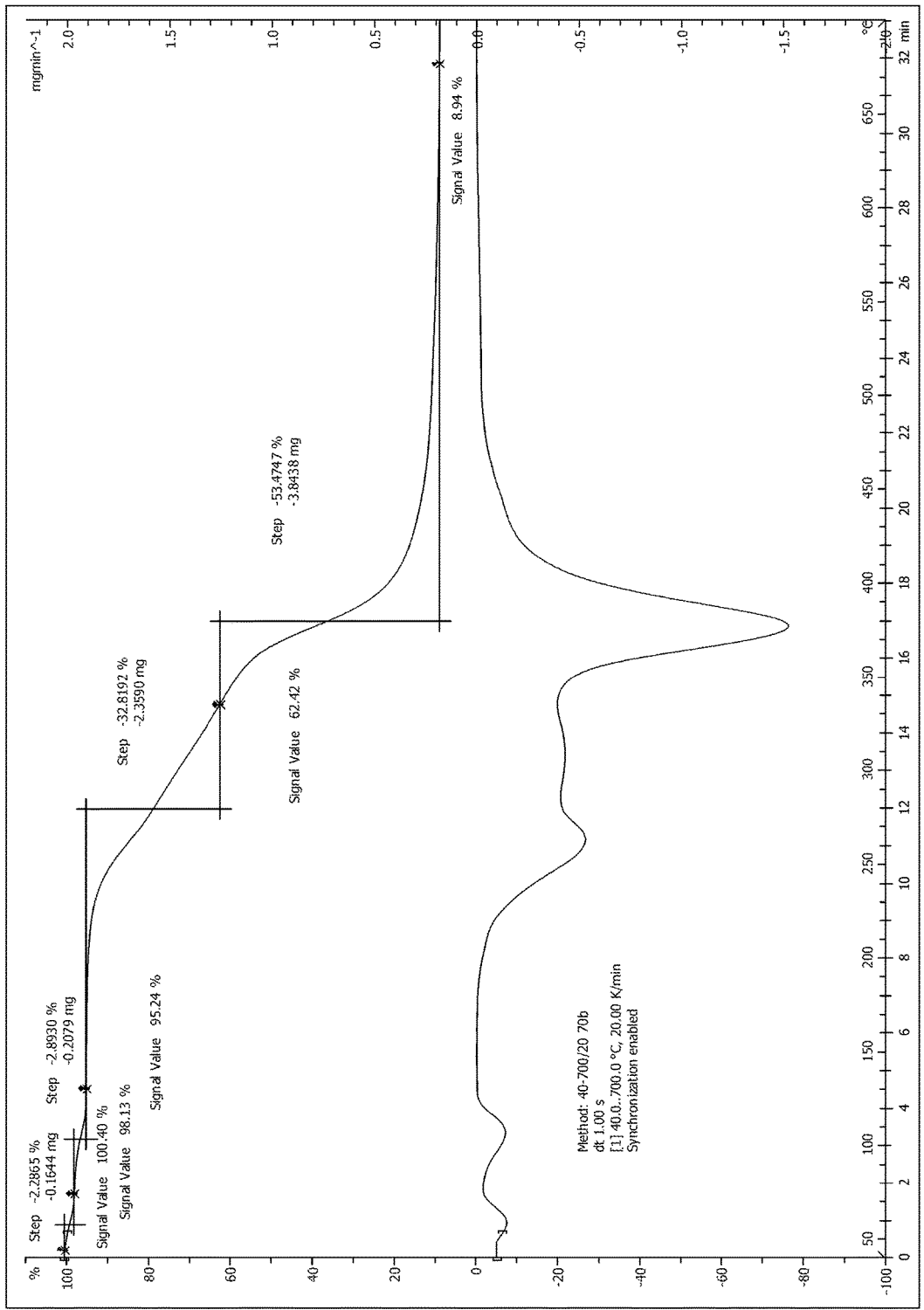
FIG. 8 shows the TGA spectrum of the solid prepared in Example 16 with 1,6-anhydro-1-C-{4-chloro-3-[(3-fluoro-4-ethoxyphenyl)methyl]phenyl}-5-C-(hydroxymethyl)-β-L-idopyranose/L-proline ratio of 1:2.

According to the same method disclosed in Example 15 of CN104031098A, 0.23 g (2 mmol) of L-proline was dissolved in 1.2 mL of 90% ethanol/water, the solution was heated to a low boil, and then a solution of 1,6-anhydro-1-C-{4-chloro-3-[(3-fluoro-4-ethoxyphenyl)methyl]phenyl}-5-C-(hydroxymethyl)-β-L-idopyranose (0.5 mmol) in 4 mL of ethanol was added. Acetone was slowly added to 5% of the total volume, the resulting solution was cooled to −20° C. for 3 hours, and a solid was formed during this time. The mixture was left for 1.5 days at room temperature. The container was centrifuged, and the supernatant was removed. The remaining solid was washed with n-hexane and dried under vacuum to obtain a white solid. HPLC analysis showed that the molar ratio of 1,6-anhydro-1-C-{4-chloro-3-[(3-fluoro-4-ethoxyphenyl)methyl]phenyl}-5-C-(hydroxymethyl)-β-L-idopyranose to L-proline was about 0.54 in the white crystalline solid. The DSC and TGA spectra of the resulting solid are shown in FIG. 7 and FIG. 8, respectively. The DSC spectrum showed that the resulting solid had three endothermic peaks at 59.55° C., 72.24° C. and 105.49° C., which suggested that this substance might be unstable and that it was possible to produce degradation at lower temperatures, thereby leading to the loss of proline from the co-crystal. The TGA spectrum showed that the weight loss of proline in the solid was 32.82% (the theoretical value is 33.4% when the molar ratio of 1,6-anhydro-1-C-{4-chloro-3-[(3-fluoro-4-ethoxyphenyl)methyl]phenyl}-5-C-(hydroxymethyl)-β-L-idopyranose to L-proline is 1:2). The analysis of the HPLC, DSC, and TGA results indicated that the molar ratio of 1,6-anhydro-1-C-{4-chloro-3-[(3-fluoro-4-ethoxyphenyl)methyl]phenyl}-5-C-(hydroxymethyl)-β-L-idopyranose to L-proline in the resulting solid product was 1:2, and the stability of the resulting product was poor.

What is claimed is:

1. Crystal form A of a complex of formula (I):

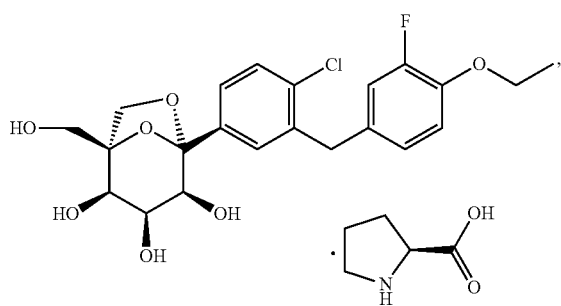

(I)

wherein the crystal is a crystal of a monohydrate, and the crystal is characterized by an X-ray powder diffraction (XRPD) spectrum comprising diffraction peaks at angles (2θ) of about 7.82, 17.28, and 18.89.

2. A preparation method of crystal form A of the complex of formula (I) according to claim 1, comprising the following steps of:
(a) dissolving 1,6-anhydro-1-C-{4-chloro-3-[(3-fluoro-4-ethoxyphenyl)methyl]phenyl}-5-C-(hydroxymethyl)-β-L-idopyranose and L-proline in a solvent to obtain a reaction solution, then cooling the reaction solution to precipitate a crystal, wherein the solvent is selected from the group consisting of an organic solvent and a mixed solvent of an organic solvent and water; and the organic solvent is one or more selected from the group consisting of alcohols, ketones, esters, ethers, hydrocarbons and nitriles having 6 or less carbon atoms; and wherein a molar ratio of L-proline and 1,6-anhydro-1-C-{4-chloro-3-[(3-fluoro-4-ethoxyphenyl)methyl]phenyl}-5-C-(hydroxymethyl)-β-L-idopyranose is less than or equal to 2:1; and
(b) filtering the crystal, then drying the crystal, thereby obtaining crystal form A of the complex of formula (I).

3. The preparation method according to claim 2, wherein the organic solvent in step (a) is methanol, ethanol, isopropanol, acetone, ethyl acetate, tetrahydrofuran, acetonitrile, or n-hexane; and the mixed solvent is methanol/water, ethanol/water, isopropanol/water, or ethanol/n-hexane.

4. The preparation method according to claim 2, wherein the method further comprises a step of recrystallizing the crystal product resulting from drying, the recrystallization solvent is selected from the group consisting of an organic solvent and a mixed solvent of an organic solvent and water; and the organic solvent is at least one selected from the group consisting of alcohols, ketones, esters, ethers, hydrocarbons and nitriles having 6 or less carbon atoms.

5. Crystal form A of a complex of formula (I):

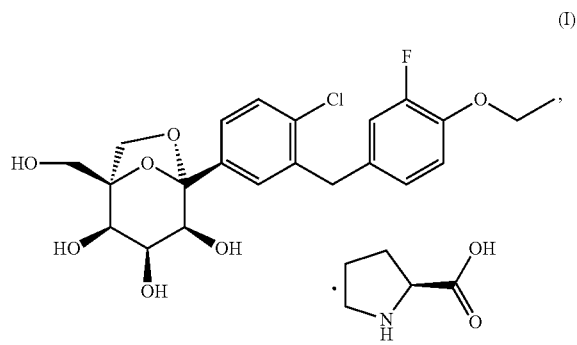

(I)

wherein the crystal form is characterized by X-ray powder diffraction (XRPD) peaks as shown in FIG. 1.

6. The crystal form A of the complex of formula (I) according to claim 1, wherein the crystal form has a differential scanning calorimetry (DSC) spectrum comprising an endothermic melting peak at about 109.5° C.

7. The crystal form A of the complex of formula (I) according to claim 1, wherein the XRPD spectrum further comprises diffraction peaks at:

| Angle (2θ) | d-value (Angstrom) |
| --- | --- |
| about 5.50 | about 16.07 |
| about 8.64 | about 10.22 |

-continued

| Angle (2θ) | d-value (Angstrom) |
|---|---|
| about 10.33 | about 8.55 |
| about 12.18 | about 7.26 |
| about 12.49 | about 7.08 |
| about 14.47 | about 6.11 |
| about 15.51 | about 5.71 |
| about 19.39 | about 4.58 |
| about 20.40 | about 4.35 |
| about 22.85 | about 3.89 |
| about 23.89 | about 3.72 |
| about 25.93 | about 3.43 |
| about 27.66 | about 3.22 |
| about 28.97 | about 3.08 and |
| about 31.16 | about 2.87. |

8. The preparation method according to claim 3, wherein the organic solvent is ethanol and the mixed solvent is ethanol/water.

9. The preparation method according to claim 4, wherein the organic solvent is methanol, ethanol, isopropanol, acetone, ethyl acetate, tetrahydrofuran, acetonitrile, or n-hexane; and the mixed solvent is methanol/water, ethanol/water, isopropanol/water, or ethanol/n-hexane.

10. A pharmaceutical composition comprising the crystal form A of the complex of formula (I) according to claim 1 and a pharmaceutically acceptable carrier.

11. A method of treating diabetes in a subject in need thereof, the method comprising administering to the subject the pharmaceutical composition according to claim 10.

12. A pharmaceutical composition comprising the crystal form A of the complex of formula (I) according to claim 5 and a pharmaceutically acceptable carrier.

13. A pharmaceutical composition comprising the crystal form A of the complex of formula (I) according to claim 7 and a pharmaceutically acceptable carrier.

14. A method of treating diabetes in a subject in need thereof, the method comprising administering to the subject the pharmaceutical composition according to claim 12.

15. A method of treating diabetes in a subject in need thereof, the method comprising administering to the subject the pharmaceutical composition according to claim 13.

16. The preparation method according to claim 2, wherein the reaction solution is heated to reflux, filtered, and then cooled to room temperature to precipitate the crystal.

17. The crystal form A of the complex of formula (I) according to claim 1, wherein the crystal form has the following d-values (angstrom) at the indicated diffraction angles (2θ):

| Angle (2θ) | d-value (Angstrom) |
|---|---|
| about 7.82 | about 11.30 |
| about 17.28 | about 5.13 and |
| about 18.89 | about 4.70. |

* * * * *